US010285925B2

(12) United States Patent
Glenn, Jr. et al.

(10) Patent No.: US 10,285,925 B2
(45) Date of Patent: *May 14, 2019

(54) METHOD OF TREATING HAIR

(71) Applicant: The Procter & Gamble Company, Cincinnati, OH (US)

(72) Inventors: Robert Wayne Glenn, Jr., Liberty Township, OH (US); Dariush Hosseinpour, Mason, OH (US); Kevin Lee Doyle, Fairfield, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/380,345

(22) Filed: Dec. 15, 2016

(65) Prior Publication Data

US 2017/0165191 A1 Jun. 15, 2017

Related U.S. Application Data

(60) Provisional application No. 62/267,583, filed on Dec. 15, 2015.

(51) Int. Cl.
| | |
|---|---|
| *A61Q 5/12* | (2006.01) |
| *A61K 8/898* | (2006.01) |
| *A61K 8/04* | (2006.01) |
| *A61K 8/06* | (2006.01) |
| *A61K 8/34* | (2006.01) |
| *A61K 8/36* | (2006.01) |
| *A61K 8/39* | (2006.01) |
| *A61K 8/41* | (2006.01) |
| *A61Q 13/00* | (2006.01) |
| *B65D 83/14* | (2006.01) |
| *A61K 8/58* | (2006.01) |

(52) U.S. Cl.
CPC ............ *A61K 8/898* (2013.01); *A61K 8/046* (2013.01); *A61K 8/068* (2013.01); *A61K 8/345* (2013.01); *A61K 8/36* (2013.01); *A61K 8/39* (2013.01); *A61K 8/416* (2013.01); *A61K 8/585* (2013.01); *A61Q 5/12* (2013.01); *A61Q 13/00* (2013.01); *B65D 83/752* (2013.01); *A61K 2800/21* (2013.01); *A61K 2800/413* (2013.01); *A61K 2800/49* (2013.01); *A61K 2800/596* (2013.01); *A61K 2800/87* (2013.01)

(58) Field of Classification Search
None
See application file for complete search history.

(56) References Cited

U.S. PATENT DOCUMENTS

| | | |
|---|---|---|
| 3,236,733 A | 2/1966 | Karsten et al. |
| 3,938,708 A | 2/1976 | Burger |
| 4,607,756 A | 8/1986 | Courtman |
| 4,610,874 A | 9/1986 | Matravers |
| 4,880,618 A | 11/1989 | Grollier et al. |
| 5,012,978 A | 5/1991 | Bolduc |
| 5,077,040 A | 12/1991 | Bergmann et al. |
| 5,635,469 A | 6/1997 | Fowler et al. |
| 5,674,478 A | 10/1997 | Dodd et al. |
| 5,985,295 A | 11/1999 | Peffly |
| 6,039,036 A | 3/2000 | Restle et al. |
| 6,589,509 B2 | 7/2003 | Keller et al. |
| 6,602,494 B1 * | 8/2003 | Jahedshoar ............ A61K 8/064 424/70.1 |
| 6,604,693 B2 | 8/2003 | Santagiuliana |
| 6,605,577 B1 | 8/2003 | Harrison et al. |
| 6,642,194 B2 | 11/2003 | Harrison et al. |
| 6,656,458 B1 | 12/2003 | Philippe et al. |
| 6,927,196 B2 | 8/2005 | Snyder et al. |
| 7,001,594 B1 | 2/2006 | Peffly et al. |
| 7,217,777 B2 | 5/2007 | Lange et al. |
| 7,316,815 B2 | 1/2008 | Philippe et al. |
| RE40,534 E | 10/2008 | Harrison et al. |
| 7,455,195 B2 | 11/2008 | Mekata |
| 7,462,585 B2 | 12/2008 | Uehara |
| 7,470,651 B2 | 12/2008 | Uehara et al. |
| 7,504,093 B2 | 3/2009 | Bracken et al. |
| 7,759,378 B2 | 7/2010 | Philippe et al. |
| 8,017,106 B2 | 9/2011 | Keller et al. |
| 8,263,053 B2 | 9/2012 | Duvel et al. |
| 8,475,777 B2 | 7/2013 | Rautschek |

(Continued)

FOREIGN PATENT DOCUMENTS

| | | |
|---|---|---|
| DE | 10304721 B4 | 3/2007 |
| EP | 978271 A1 | 2/2000 |

(Continued)

OTHER PUBLICATIONS

U.S. Appl. No. 15/380,194, filed Dec. 15, 2016, Glenn, Jr. et al.
U.S. Appl. No. 15/380,218, filed Dec. 15, 2016, Glenn, Jr. et al.
U.S. Appl. No. 15/380,261, filed Dec. 15, 2016, Glenn, Jr. et al.
U.S. Appl. No. 15/380,293, filed Dec. 15, 2016, Glenn, Jr. et al.
U.S. Appl. No. 15/380,373, filed Dec. 15, 2016, Glenn, Jr. et al.
U.S. Appl. No. 15/492,429, filed Apr. 20, 2017, Glenn, Jr. et al.
U.S. Appl. No. 15/492,451, filed Apr. 20, 2017, Glenn, Jr. et al.
U.S. Appl. No. 15/492,469, filed Apr. 20, 2017, Glenn, Jr. et al.
U.S. Appl. No. 15/381,298, filed Dec. 16, 2016, Callens et al.
U.S. Appl. No. 62/435,267, filed Dec. 16, 2016, Glenn, Jr. et al.
U.S. Appl. No. 62/435,271, filed Dec. 16, 2016, Glenn, Jr. et al.

(Continued)

*Primary Examiner* — Jyothsna A Venkat
(74) *Attorney, Agent, or Firm* — Alexandra S. Anoff

(57) ABSTRACT

A method of treating the hair including providing a concentrated hair care composition in a mechanical foam dispenser. The concentrated hair care composition includes one or more silicones, from about 1% to about 5% perfume, an emulsifier system, and is substantially free of high melting point fatty compounds. The method also includes dispensing the concentrated hair care composition from the mechanical foam dispenser as a dosage of foam; applying the foam to the hair; and rinsing the foam from the hair. The foam has a density of from about 0.025 g/cm³ to about 0.3 g/cm³ when dispensed from the mechanical foam dispenser.

15 Claims, No Drawings

(56) References Cited

U.S. PATENT DOCUMENTS

| | | |
|---|---|---|
| 8,476,472 B2 | 7/2013 | Hojo et al. |
| 8,642,021 B2 | 2/2014 | Brautigam et al. |
| 8,697,040 B2 | 4/2014 | Duvel et al. |
| 8,956,597 B2 | 2/2015 | Gesztesi et al. |
| 8,999,306 B2 | 4/2015 | Duvel et al. |
| 9,255,184 B2 | 2/2016 | Paul |
| 9,308,398 B2 | 4/2016 | Hutton et al. |
| 9,358,186 B2 | 6/2016 | Chandra et al. |
| 9,539,199 B2 | 1/2017 | Beer et al. |
| 9,539,208 B2 | 1/2017 | Tamarkin et al. |
| 9,540,489 B2 | 1/2017 | Panandiker et al. |
| 9,828,170 B2 | 11/2017 | Nomura et al. |
| 9,993,419 B2 | 6/2018 | Glenn, Jr. et al. |
| 2001/0008630 A1 | 7/2001 | Pyles et al. |
| 2001/0025857 A1 | 10/2001 | Baudin |
| 2002/0031532 A1 | 3/2002 | Uchiyama |
| 2002/0143063 A1 | 10/2002 | Alvarado |
| 2002/0197213 A1 | 12/2002 | Schmenger et al. |
| 2003/0152542 A1 | 8/2003 | Decoster et al. |
| 2003/0228272 A1 | 12/2003 | Amjad et al. |
| 2004/0018164 A1 | 1/2004 | Zofchak et al. |
| 2004/0076595 A1* | 4/2004 | Khan ............... A61K 8/06 424/70.11 |
| 2004/0229763 A1 | 11/2004 | Hutton, III et al. |
| 2004/0247550 A1 | 12/2004 | Asari et al. |
| 2005/0002892 A1 | 1/2005 | Khan et al. |
| 2005/0136011 A1 | 6/2005 | Nekludoff et al. |
| 2005/0196372 A1 | 9/2005 | Cajan |
| 2005/0196376 A1 | 9/2005 | Loomis |
| 2005/0197421 A1 | 9/2005 | Loomis |
| 2005/0222001 A1 | 10/2005 | Baumeister et al. |
| 2005/0274737 A1 | 12/2005 | Krause et al. |
| 2006/0034792 A1 | 2/2006 | Lazzeri et al. |
| 2006/0054634 A1 | 3/2006 | Mekata |
| 2006/0083704 A1 | 4/2006 | Torgerson |
| 2006/0275245 A1 | 12/2006 | Decoster et al. |
| 2006/0292104 A1 | 12/2006 | Guskey et al. |
| 2006/0293197 A1 | 12/2006 | Uehara et al. |
| 2007/0179207 A1 | 8/2007 | Fernandez de Castro et al. |
| 2007/0286837 A1 | 12/2007 | Torgerson |
| 2008/0066773 A1 | 3/2008 | Anderson et al. |
| 2008/0138296 A1 | 6/2008 | Tamarkin et al. |
| 2008/0292560 A1 | 11/2008 | Tamarkin et al. |
| 2008/0292574 A1 | 11/2008 | Uehara |
| 2009/0041706 A1 | 2/2009 | Molenda et al. |
| 2009/0155383 A1 | 6/2009 | Kitko et al. |
| 2009/0232759 A1 | 9/2009 | Bell et al. |
| 2010/0092405 A1 | 4/2010 | Philippe et al. |
| 2010/0143280 A1 | 6/2010 | Yokogi et al. |
| 2010/0143281 A1 | 6/2010 | Okada et al. |
| 2010/0143282 A1 | 6/2010 | Yokogi et al. |
| 2010/0143425 A1 | 6/2010 | Okada et al. |
| 2010/0178265 A1* | 7/2010 | Molenda ............. A61K 8/49 424/70.9 |
| 2011/0135588 A1 | 6/2011 | Uehara et al. |
| 2011/0226273 A1 | 9/2011 | Deardorff et al. |
| 2011/0280110 A1 | 11/2011 | Chen |
| 2011/0318295 A1 | 12/2011 | Shimizu |
| 2012/0020908 A1 | 1/2012 | Paul |
| 2012/0034173 A1 | 2/2012 | Batt et al. |
| 2012/0043352 A1 | 2/2012 | Rasmussen et al. |
| 2012/0114819 A1 | 5/2012 | Ragnarsson |
| 2012/0171147 A1 | 7/2012 | Rautschek |
| 2012/0288465 A1 | 11/2012 | Loechel |
| 2013/0075430 A1 | 3/2013 | Ragnarsson |
| 2013/0202666 A1 | 8/2013 | Petkov et al. |
| 2013/0280192 A1 | 10/2013 | Carter et al. |
| 2013/0284196 A1 | 10/2013 | Murdock et al. |
| 2014/0105943 A1 | 4/2014 | Pistoria et al. |
| 2014/0107224 A1 | 4/2014 | Osman et al. |
| 2014/0116458 A1 | 5/2014 | Krueger |
| 2014/0135414 A1 | 5/2014 | Loomis |
| 2014/0237732 A1 | 8/2014 | Zuedel Fernandes et al. |
| 2014/0261517 A1 | 9/2014 | Humphreys et al. |
| 2014/0302103 A1 | 10/2014 | Carter et al. |
| 2014/0356303 A1 | 12/2014 | Rocco et al. |
| 2014/0377206 A1 | 12/2014 | Uehara et al. |
| 2015/0011450 A1 | 1/2015 | Carter et al. |
| 2015/0030643 A1 | 1/2015 | Gartstein et al. |
| 2015/0093420 A1 | 4/2015 | Snyder et al. |
| 2015/0190326 A1 | 7/2015 | Brouard et al. |
| 2015/0359725 A1 | 12/2015 | Glenn, Jr. et al. |
| 2015/0359726 A1 | 12/2015 | Glenn, Jr. et al. |
| 2015/0359727 A1 | 12/2015 | Glenn, Jr. et al. |
| 2015/0359728 A1 | 12/2015 | Glenn, Jr. et al. |
| 2016/0000673 A1 | 1/2016 | Ainger et al. |
| 2016/0310375 A1 | 4/2016 | Torres Rivera et al. |
| 2016/0310376 A1 | 4/2016 | Torres Rivera et al. |
| 2016/0143821 A1 | 5/2016 | Chang et al. |
| 2016/0309871 A1 | 10/2016 | Torres Rivera et al. |
| 2016/0310371 A1 | 10/2016 | Zhao et al. |
| 2016/0310372 A1 | 10/2016 | Glenn, Jr. et al. |
| 2016/0310377 A1 | 10/2016 | Torres Rivera et al. |
| 2016/0310397 A1 | 10/2016 | Johnson et al. |
| 2017/0087068 A1 | 3/2017 | Callens et al. |
| 2017/0165155 A1 | 6/2017 | Glenn, Jr. et al. |
| 2017/0165156 A1 | 6/2017 | Glenn, Jr. et al. |
| 2017/0165157 A1 | 6/2017 | Glenn, Jr. et al. |
| 2017/0165162 A1 | 6/2017 | Glenn, Jr. et al. |
| 2017/0165163 A1 | 6/2017 | Glenn, Jr. et al. |
| 2017/0165191 A1 | 6/2017 | Glenn, Jr. et al. |
| 2017/0174413 A1 | 6/2017 | Callens et al. |
| 2017/0304184 A1 | 10/2017 | Glenn, Jr. et al. |
| 2017/0304185 A1 | 10/2017 | Glenn, Jr. et al. |
| 2017/0304186 A1 | 10/2017 | Glenn, Jr. et al. |
| 2018/0168948 A1 | 6/2018 | Glenn, Jr. et al. |
| 2018/0168949 A1 | 6/2018 | Glenn, Jr. et al. |
| 2018/0168996 A1 | 6/2018 | Glenn, Jr. et al. |
| 2018/0221270 A1 | 8/2018 | Glenn, Jr. et al. |
| 2018/0256457 A1 | 9/2018 | Glenn, Jr. et al. |
| 2018/0256459 A1 | 9/2018 | Torres Rivera et al. |
| 2018/0256481 A1 | 9/2018 | Glenn, Jr. et al. |
| 2018/0353398 A1 | 12/2018 | Torres Rivera et al. |

FOREIGN PATENT DOCUMENTS

| | | | |
|---|---|---|---|
| EP | 1002525 | A2 | 5/2000 |
| EP | 1340485 | A2 | 2/2003 |
| EP | 2138155 | A2 | 12/2009 |
| EP | 2883533 | * | 6/2015 |
| JP | H06227941 | A | 8/1994 |
| JP | 2001302466 | A | 10/2001 |
| JP | 3242689 | B2 | 12/2001 |
| JP | 2003-119113 | A | 4/2003 |
| JP | 2005232271 | A | 9/2005 |
| JP | 2006182743 | A | 7/2006 |
| JP | 2010-132569 | A | 6/2010 |
| JP | 4694171 | B2 | 6/2011 |
| JP | 2014-125477 | A | 7/2014 |
| WO | WO 96/19188 | A1 | 6/1996 |
| WO | WO 97/20626 | A1 | 6/1997 |
| WO | WO0222085 | A1 | 3/2002 |
| WO | WO 2004/078901 | A1 | 9/2004 |
| WO | WO2006045170 | A2 | 5/2006 |
| WO | WO 2013/176666 | A1 | 11/2013 |

OTHER PUBLICATIONS

U.S. Appl. No. 62/435,296, filed Dec. 16, 2016, Glenn, Jr. et al.
All Office Actions, U.S. Appl. No. 14/739,588.
All Office Actions, U.S. Appl. No. 14/739,670.
All Office Actions, U.S. Appl. No. 14/739,708.
All Office Actions, U.S. Appl. No. 14/739,755.
All Office Actions, U.S. Appl. No. 15/135,684.
All Office Actions, U.S. Appl. No. 15/135,691.
All Office Actions, U.S. Appl. No. 15/135,705.
All Office Actions, U.S. Appl. No. 15/135,715.
All Office Actions, U.S. Appl. No. 15/380,194.
All Office Actions, U.S. Appl. No. 15/380,218.
All Office Actions, U.S. Appl. No. 15/380,261.
All Office Actions, U.S. Appl. No. 15/380,293.
All Office Actions, U.S. Appl. No. 15/380,373.

(56) References Cited

OTHER PUBLICATIONS

All Office Actions, U.S. Appl. No. 15/135,712.
All Office Actions, U.S. Appl. No. 15/274,226.
All Office Actions, U.S. Appl. No. 15/381,298.
All Office Actions, U.S. Appl. No. 15/136,020.
All Office Actions, U.S. Appl. No. 15/136,032.
All Office Actions, U.S. Appl. No. 15/492,429.
All Office Actions, U.S. Appl. No. 15/492,451.
All Office Actions, U.S. Appl. No. 15/492,469.
Carolyn Evans: "Scalp Cleansing, Scalp Tonique, Hair Shampoo, Hair Conditioner, Demonstration" Youtube, Apr. 22, 2012, p. 2. First part of the video (0-3 min) dedicated to "scalp cleansing"; second part of the video (3-6 min) dedicated to the treatment of the hair.
Anonymous: "GNPD—Anti-Dandruff Shampoo", Nov. 1, 2012.
Anonymous "Shampoo only Scalp? Or entire head?—The Long Hair Community Discussion Boards", Feb. 1, 2011, Retrieved from the internet: URL: http://forums.longhaircommunity.com/archieve/index.php/t-91788.html, retrieved on Jul. 21, 2016.
Samantha Zabell: "Mistakes You're Making Washing Your Hair—How You're Washing Your Hair Wrong", Jan. 14, 2014, Retrieved from the Internet: URL: http://www.goodhousekeeping.com/beauty/hair/tips/a19894/mistakes-washing-your-hair/, Section 3. "Overdoing it on shampoo and/or conditioner"; p. 2, retrieved on Jul. 21, 2016.
Anonymous: "GNPD—Anti-Dandruff Shampoo + Conditioner Set", Procter and Gamble China, Apr. 1, 2009, Mintel GNPD, Retrieved from the Internet: URL: http://www.gnpd.com/sinatra/recordpage/107827/from_search/EkXVQ1u6vF/?page=2, Retrieved on Jul. 12, 2016.
Database GNPD, Mintel; Aug. 2014 "Gold Olive Haircare Set".
Database GNPD Mintel; May 2014, "Coconut & Macadamia Oil Nourishing Shampoo and Nourishing Conditioner".
"Clarifying Shampoo", Mintel, Jun. 2015.
"Reinforcing conditioner", Mintel, May 2014.
Silsoft* 251, amine functional silicone microemulsion, Momentive Marketing Bulletin, 2012, 2 pages.
In-Cosmetics 2012: Wacker Introduced Novel Silicone Emulsions and New Hybrid Polymer for Hair-Care and Hair-Styling Products, Apr. 17, 2012, Munich.
PCT International Search Report and Written Opinion for PCT/US2016/066753 dated Feb. 28, 2017, 11 pages.
PCT International Search Report and Written Opinion for PCT/US2016/067916 dated Mar. 29, 2016.
PCT International Search Report and Written Opinion for PCT/US2016/028731 dated Jul. 5, 2016, 11 pages.
PCT International Search Report and Written Opinion for PCT/US2016/028860 dated Jul. 7, 2016, 11 pages.
PCT International Search Report and Written Opinion for PCT/US2015/035796 dated Sep. 14, 2015, 9 pages.
PCT International Search Report and Written Opinion for PCT/US2015/035756 dated Dec. 21, 2015, 13 pages.
PCT International Search Report and Written Opinion for PCT/US2015/035797 dated Sep. 14, 2015, 9 pages.
PCT International Search Report and Written Opinion for PCT/US2015/035799 dated Sep. 14, 2015, 9 pages.
PCT International Search Report and Written Opinion for PCT/US2016/028739 dated Jul. 4, 2016, 11 pages.
PCT International Search Report and Written Opinion for PCT/US2016/066755 dated Feb. 27, 2017, 12 pages.
PCT International Search Report and Written Opinion for PCT/US2016/066759 dated Feb. 27, 2017, 11 pages.
PCT International Search Report and Written Opinion for PCT/US2016/066754 dated Feb. 20, 2017, 11 pages.
PCT International Search Report and Written Opinion for PCT/US2016/028745 dated Aug. 8, 2016.
PCT International Search Report and Written Opinion for PCT/US2016/028853 dated Sep. 30, 2016, 19 pages.
PCT International Search Report and Written Opinion for PCT/US2016/028855, dated Oct. 5, 2016, 18 pages.
PCT International Search Report and Written Opinion for PCT/US2016/028743 dated Jul. 25, 2016.
U.S. Appl. No. 15/843,069, filed Dec. 15, 2017, Glenn, Jr. et al.
U.S. Appl. No. 15/843,146, filed Dec. 15, 2017, Glenn, Jr. et al.
U.S. Appl. No. 15/843,178, filed Dec. 15, 2017, Glenn, Jr. et al.
All final and non-final office actions for U.S. Appl. No. 15/843,069.
All final and non-final office actions for U.S. Appl. No. 15/843,146.
All final and non-final office actions for U.S. Appl. No. 15/843,178.
Fabida. https://makeupandbeauty.com/head-shoulders-anti-dandruff-itchy-scalp-care-shampoo-review/. Published Jun. 26, 2012.
Free Sample. https://web.archive.org/web/20111116042029/http://freesampleprincess.com/head-and-shoulders-itchy-scalp-care-free-sample. Published Nov. 16, 2011.
Hair Conditioner Tips and Tricks. https://web.archive.org/web/20121106125731/http://www.thehairstyler.com/features/articles/hair-care/hair-conditioner-tips-and-tricks. Published Nov. 6, 2012.
Mommy Story, http://www.amommystory.com/2011/11/head-shoulders-eucalyptus-itchy-scalp-care-to-the-rescue-review-giveaway.html. Published Nov. 21, 2011.
PCT International Search Report and Written Opinion for PCT/US2017/028472 dated Jun. 29, 2017.
PCT International Search Report and Written Opinion for PCT/US2017/028473 dated Jun. 29, 2017.
PCT International Search Report and Written Opinion for PCT/US2017/028474 dated Jun. 29, 2017.
Stylecaster. http://stylecaster.com/beauty/how-to-get-rid-of-dandruff/. Published: Jan. 16, 2014.
Xiameter Mem-0949 Emulsion (Nov. 2011).
U.S. Appl. No. 15/978,667, filed May 14, 2018, Glenn, Jr. et al.
U.S. Appl. No. 15/972,763, filed May 7, 2018, Torres Rivera et al.
U.S. Appl. No. 16/104,343, filed Aug. 17, 2018, Torres Rivera et al.
U.S. Appl. No. 15/946,275, filed Apr. 5, 2018, Glenn, Jr. et al.
U.S. Appl. No. 15/973,845, filed May 8, 2018, Glenn, Jr. et al.
All final and non-final office actions for U.S. Appl. No. 15/946,275.
All final and non-final office actions for U.S. Appl. No. 15/972,763.
All final and non-final office actions for U.S. Appl. No. 15/973,845.
All final and non-final office actions for U.S. Appl. No. 15/978,667.
All final and non-final office actions for U.S. Appl. No. 16/104,343.
All final and non-final Office Actions, U.S. Appl. No. 15/135,715.
PCT International Search Report and Written Opinion for PCT/US2017/066561 dated Apr. 4, 2018.
PCT International Search Report and Written Opinion for PCT/US2017/066563 dated Apr. 4, 2018.

* cited by examiner

METHOD OF TREATING HAIR

FIELD OF THE INVENTION

Described herein is a method of treating hair with a concentrated hair care composition comprising an emulsifier system provided in a mechanical foam dispenser.

BACKGROUND OF THE INVENTION

Today's hair conditioners almost universally comprise high levels of high melting point fatty compounds, the most common of which are C16 to C18 fatty alcohols. These high melting point fatty compounds are employed as structuring agents wherein they are combined with one or more surfactants and an aqueous carrier to form a gel network. The gel network increases the viscosity and yield point which facilitates the dispensing of the conditioner from a bottle or tube and the subsequent distribution and spreading of the product through the hair by the consumer. The structuring of the product via gel network also enables incorporation of silicones, perfumes and oils in the form of an oil-in-water emulsion that is phase stable. These silicones and oils are intended to be deposited on the hair to provide the primary hair conditioning benefits including wet and dry combing friction reduction and hair manageability etc.

However, today's gel network hair conditioners lead to excessive co-deposits of the high melting point fatty compound on the hair over multiple cycles. Additionally, the deposited high melting point fatty compounds build-up on hair over multiple cycles and lead to significant waxy build-up on hair and hair weigh down. Indeed, one of the major consumer complaints with hair conditioners is waxy residue which makes hair look greasy or feel heavy. Many current gel network hair conditioners deposit up to 10 times more high melting point fatty compounds (fatty alcohols) than silicone or oil after approximately 10 treatment cycles in technical testing. While not being bound to theory, this is hypothesized to be due to the ~10× greater concentration of high melting point weight fatty compounds in the product relative to the silicone or oil. Such a high level of melting point fatty compounds (fatty alcohols) may be required to produce a shelf stable gel network with sufficient structuring for consumer acceptable viscosity and rheology.

Described herein is a concentrated hair care composition that enables new product opportunities and consumer benefits by addressing the current disadvantages associated with gel network conditioners. It has been found that concentrated and ultra-low viscosity hair conditioner compositions can be delivered to the hair in foamed form with lower dosage (due to lower foam density). These inventive compositions are concentrated to enable sufficient dosage from a foam delivery form while also eliminating the need for high melting point fatty compounds or other "insoluble" structurants that can lead to significant co-deposits (from wax structured to gas structured), build-up and weigh down of hair. The inventive compositions are also nano-emulsions to help enable shelf stability at the lower viscosities required for foaming The net result has been a step change improvement in silicone deposition purity versus today's rinse-off products and an improvement in technical performance benefits from such a more pure and transparent deposited silicone layer. These benefits include multicycle hair conditioning without hair weigh down, durable conditioning, reduced hair dye fade, and increased color vibrancy.

Nanoemulsion technology development is hindered by complex stability issues that emerge when droplet sizes are driven to the nanoscale. This may be especially problematic in the presence of higher levels of perfume oils which may be required for such a concentrated product. The concentrated hair care composition described herein is therefore also focused on improved stability via the development of a specific emulsifier system.

SUMMARY OF THE INVENTION

Described herein is a method of treating the hair, the method comprising (a) providing a concentrated hair care composition in a mechanical foam dispenser, wherein the concentrated hair care composition comprises (i) from about 3% to about 25% of one or more silicones, by weight of the concentrated hair care composition, wherein the particle size of the one or more silicones is from about 1 nm to about 100 nm; (ii) from about 1% to about 5% perfume, by weight of the concentrated hair care composition; (iii) an emulsifier system comprising (1) from about 1% to about 10% of one or more Type I emulsifiers by weight of the concentrated hair care composition, the one or more Type I emulsifiers having from about 5 to about 9 moles of ethoxylate, the one or more Type I emulsifiers having an HLB value of from about 10.3 to about 13; (2) from about 0.5% to about 5% of one or more Type II emulsifiers by weight of the concentrated hair care composition, the one or more Type II emulsifiers having from about 2 to about 4.9 moles of ethoxylate, the one or more Type II emulsifiers having an HLB value of from about 8 to about 10.3; and (iv) from about 60% to about 90% water, by weight of the concentrated hair care composition; wherein the concentrated hair care composition is substantially free of one or more high melting point fatty compounds; wherein the concentrated hair care composition has a liquid phase viscosity of from about 1 centipoise to about 80 centipoise; wherein the concentrated hair care composition has a silicone to high melting point fatty compound ratio of about 100:0, by weight of the silicone and by weight of the high melting point fatty compound; and wherein the concentrated hair care composition has a silicone to perfume ratio of from about 95:5 to about 50:50, by weight of the silicone and by weight of the perfume; (b) dispensing the concentrated hair care composition from the mechanical foam dispenser as a dosage of foam; (c) applying the foam to the hair; and (d) rinsing the foam from the hair; wherein the foam has a density of from about 0.025 g/cm$^3$ to about 0.3 g/cm$^3$ when dispensed from the mechanical foam dispenser.

Also described herein is a mechanical foam dispenser comprising a concentrated hair care composition, the concentrated hair care composition comprising (a) from about 3% to about 25% of one or more silicones, by weight of the concentrated hair care composition, wherein the particle size of the one or more silicones is from about 1 nm to about 100 nm; (b) from about 1% to about 5% perfume, by weight of the concentrated hair care composition; and (c) an emulsifier system comprising (i) from about 1% to about 10% of one or more Type I emulsifiers by weight of the concentrated hair care composition, the one or more Type I emulsifiers having from about 5 to about 9 moles of ethoxylate, the one or more Type I emulsifiers having an HLB value of from about 10.3 to about 13; (ii) from about 0.5% to about 5% of one or more Type II emulsifiers by weight of the concentrated hair care composition, the one or more Type II emulsifiers having from about 2 to about 4.9 moles of ethoxylate, the one or more Type II emulsifiers having an HLB value of from about 8 to about 10.3; and wherein the concentrated hair care composition is substantially free of high melting point fatty compounds; wherein the concentrated hair care composition has a liquid phase viscosity of from about 1 centipoise to about 80 centipoise; wherein the concentrated hair care composition has a silicone to high melting point fatty compound ratio of about 100:0, by weight of the silicone and by weight of the high melting point fatty compound; wherein the concentrated hair care composition has a silicone to perfume ratio of from about 95:5 to about 50:50, by weight of the silicone and by weight of the high melting point fatty compound; wherein the foam has a density of from about 0.025 g/cm$^3$ to about 0.3 g/cm$^3$ when dispensed from the mechanical foam dispenser; and wherein the concentrated hair care composition is rinse-off.

DETAILED DESCRIPTION OF THE INVENTION

While the specification concludes with claims particularly pointing out and distinctly claiming the invention, it is believed that the present invention will be better understood from the following description.

As used herein, the articles including "a" and "an" when used in a claim, are understood to mean one or more of what is claimed or described.

As used herein, "comprising" means that other steps and other ingredients which do not affect the end result can be added. This term encompasses the terms "consisting of" and "consisting essentially of".

As used herein, "mixtures" is meant to include a simple combination of materials and any compounds that may result from their combination.

As used herein, "molecular weight" or "M.Wt." refers to the weight average molecular weight unless otherwise stated.

As used herein, the terms "include," "includes," and "including," are meant to be non-limiting and are understood to mean "comprise," "comprises," and "comprising," respectively.

As used herein, the term "concentrated" means a hair care composition comprising from about 3% to about 25% of one or more silicones, by weight of the hair care composition.

As used herein, the term "nanoemulsion" means an oil-in-water (o/w) emulsion with an average particle size ranging from about 1 nm to about 100 nm. The particle size referred to herein is z-average measured by dynamic light scattering. The nanoemulsion described herein may be prepared by the following methods: (1) mechanically breaking down the emulsion droplet size; (2) spontaneously forming the emulsion (may be referred to as a microemulsion in the literature); and (3) using emulsion polymerization to achieve average particle size in the target range described herein.

All percentages, parts and ratios are based upon the total weight of the compositions of the present invention, unless otherwise specified. All such weights as they pertain to listed ingredients are based on the active level and, therefore, do not include carriers or by-products that may be included in commercially available materials.

Unless otherwise noted, all component or composition levels are in reference to the active portion of that component or composition, and are exclusive of impurities, for example, residual solvents or by-products, which may be present in commercially available sources of such components or compositions.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Hair Care Composition

The method of treating the hair described herein comprises providing a concentrated hair care composition in a mechanical foam dispenser. The concentrated hair care composition may comprise one or more silicones and perfume.

A. Silicone Deposition Purity

The method of treating hair comprises dispensing the concentrated hair care composition described herein from the mechanical foam dispenser as a dosage of foam. The foam may comprise a silicone deposition purity of from about 90% to about 100% after applying the foam to the hair and rinsing the foam from the hair.

Deposition Purity can be determined by the ratio of silicone deposited per weight of hair to the total deposition of other ingredients per weight of hair. The amount of silicone is determined by either extraction or digestion of the hair followed by an analysis with a quantitative technique such as gas chromatography. The total deposition may be determined by the sum of separate deposition measurements or by a Single Inclusive Measurement of total deposition. The separate deposition measurements may include but are not limited to fatty alcohols, EGDS, quaternized agents, and silicone. Typically these measurements involve extracting the hair then separating the ingredients of interest with chromatography and quantifying with an externally calibration based on test solution concentration. The Single Inclusive Measurement of total deposition is gravimetric. The hair is thoroughly extracted and the residue determined by weighing the dissolved residue in the extract after evaporating the solvent. This residue contains both deposited ingredients and naturally occurring extractable compounds from the hair (primarily lipids). The naturally occurring extractable compounds are quantified and subtracted from the total. These include: fatty acids, squalene, cholesterol, ceramides, wax esters, triglycerides and sterol esters. The method of quantitation is similar to the deposition measurements. Other supporting evidence of Deposition Purity may include spectroscopic or topography mapping of the hair surface.

B. Silicones

The concentrated hair care composition may comprise from about 5% to about 20%, alternatively from about 8% to about 18%, and alternatively from about 10% to about 14% of one or more silicones, by weight of the concentrated hair care composition. In a further embodiment, the hair care composition may comprise from about 3% to about 25%, alternatively from about 4% to about 20%, alternatively from about 5% to about 15% of one or more silicones, and alternatively from about 6% to about 12% by weight of the concentrated hair care composition. In one embodiment, the hair care composition may comprise from about 8% to about 15% of one or more silicones. The particle size of the one or more silicones may be from about 1 nm to about 100 nm, alternatively from about 5 nm to about 80 nm, alternatively from about 10 nm to about 60 nm, and alternatively from about 12 nm to about 50 nm. In a further embodiment, the particle size of the one or more silicones may be from about 1 nm to about 500 nm, alternatively from about 5 nm to about 300 nm, alternatively from about 8 nm to about 200 nm, and alternatively from about 10 nm to about 100 nm. In an embodiment, the silicone is an aminosilicone comprising from about 0.7% to about 1.3% nitrogen content.

The particle size of the one or more silicones can be measured by dynamic light scattering (DLS) using a 173° measurement angle and the refractive index of the one or more silicones. A Malvern Zetasizer Nano ZEN3600 system (www.malvern.com) using He—Ne laser 633 nm can be used for the measurement at 25° C.

The Zetasizer Software provided by Malvern Instruments, was used for data analysis. For each sample, 3 measurements were made and Z-average values were reported as the particle size.

In an embodiment, the one or more silicones may be in the form of a nanoemulsion. A nanoemulsion, as defined herein, may be an emulsion wherein the particle size is below 100 nm. The nanoemulsion may comprise any silicone suitable for application to the skin and/or hair. In one embodiment, from about 25% to about 100% of the one or more silicones is in the form of a nanoemulsion, in another embodiment from about 50% to about 100% of the one or more silicones is in the form of a nanoemulsion, and in another embodiment from about 75% to about 100% of the one or more silicones is in the form of a nanoemulsion.

In an embodiment, the one or more silicones may include in their molecular structure polar functional groups such as Si—OH (present in dimethiconols), primary amines, secondary amines, tertiary amines, and quaternary ammonium salts. The one or more silicones may be selected from the group consisting of aminosilicones, pendant quaternary ammonium silicones, terminal quaternary ammonium silicones, amino polyalkylene oxide silicones, quaternary ammonium polyalkylene oxide silicones, and amino morpholino silicones.

The one or more silicones may comprise:
(a) at least one aminosilicone corresponding to formula (V):

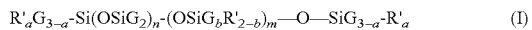

in which:
G is chosen from a hydrogen atom, a phenyl group, OH group, and $C_1$-$C_8$ alkyl groups, for example methyl,
a is an integer ranging from 0 to 3, and in one embodiment a is 0,
b is chosen from 0 and 1, and in one embodiment b is 1,
m and n are numbers such that the sum (n+m) can range for example from 1 to 2 000, such as for example from 50 to 150, wherein n can be for example chosen from numbers ranging from 0 to 1 999, such as for example from 49 to 149, and wherein m can be chosen from numbers ranging for example from 1 to 2 000, such as for example from 1 to 10;
R' is a monovalent group of formula —$C_qH_{2q}$L in which q is a number from 2 to 8 and L is an optionally quaternized amine group chosen from the groups:
—NR"—$CH_2$—$CH_2$—N'($R^1$)$_2$,
—N(R")$_2$,
—$N^+$(R")$_3A^-$,
—$N^+$H(R")$_2A^-$,
—$N^+H_2$(R")$A^-$, and
—N(R")—$CH_2$—$CH_2$—$N^+R"H_2A^-$,
in which R" can be chosen from a hydrogen atom, phenyl groups, benzyl groups, and saturated monovalent hydrocarbon-based groups, such as for example an alkyl group comprising from 1 to 20 carbon atoms, and $A^-$ is chosen from halide ions such as, for example, fluoride, chloride, bromide and iodide.

In an embodiment, the one or more silicones may include those corresponding to formula (1) wherein a=0, G=methyl, m and n are numbers such that the sum (n+m) can range for example from 1 to 2 000, such as for example from 50 to 150, wherein n can be for example chosen from numbers ranging from 0 to 1 999, such as for example from 49 to 149, and wherein m can be chosen from numbers ranging for example from 1 to 2 000, such as for example from 1 to 10; and L is —N(CH$_3$)$_2$ or —NH$_2$, alternatively —NH$_2$.

Additional said at least one aminosilicone of the invention include:
(b) pendant quaternary ammonium silicones of formula (VII):

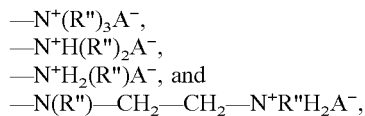

in which:
$R_5$ is chosen from monovalent hydrocarbon-based groups comprising from 1 to 18 carbon atoms, such as $C_1$-$C_{18}$ alkyl groups and $C_2$-$C_{18}$ alkenyl groups, for example methyl;
$R_6$ is chosen from divalent hydrocarbon-based groups, such as divalent $C_1$-$C_{18}$ alkylene groups and divalent $C_1$-$C_{18}$ alkylenoxy groups, for example $C_1$-$C_8$ alkylenoxy groups, wherein said $R_6$ is bonded to the Si by way of an SiC bond;
$Q^-$ is an anion that can be for example chosen from halide ions, such as chloride, and organic acid salts (such as acetate);
r is an average statistical value ranging from 2 to 20, such as from 2 to 8;
s is an average statistical value ranging from 20 to 200, such as from 20 to 50.

Such aminosilicones are described more particularly in U.S. Pat. No. 4,185,087, the disclosure of which is incorporated by reference herein.

A silicone which falls within this class is the silicone sold by the company Union Carbide under the name "Ucar Silicone ALE 56".

Further examples of said at least one aminosilicone include:
c) quaternary ammonium silicones of formula (VIIb):

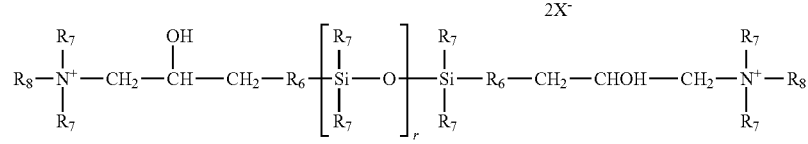

in which:
groups $R_7$, which may be identical or different, are each chosen from monovalent hydrocarbon-based groups comprising from 1 to 18 carbon atoms, such as $C_1$-$C_{18}$ alkyl groups, for example methyl, $C_2$-$C_{18}$ alkenyl groups, and rings comprising 5 or 6 carbon atoms;

$R_6$ is chosen from divalent hydrocarbon-based groups, such as divalent $C_1$-$C_{18}$ alkylene groups and divalent $C_1$-$C_{18}$ alkylenoxy, for example $C_1$-$C_8$, group connected to the Si by an SiC bond;

$R_8$, which may be identical or different, represent a hydrogen atom, a monovalent hydrocarbon-based group comprising from 1 to 18 carbon atoms, and in particular a $C_1$-$C_{18}$ alkyl group, a $C_2$-$C_{18}$ alkenyl group or a group —$R_6$—NHCOR$_7$;

$X^-$ is an anion such as a halide ion, in particular chloride, or an organic acid salt (acetate, etc.);

r represents an average statistical value from 2 to 200 and in particular from 5 to 100.

Such silicones are described, for example, in application EP-A-0 530 974, the disclosure of which is incorporated by reference herein.

Silicones falling within this class are the silicones sold by the company Goldschmidt under the names Abil Quat 3270, Abil Quat 3272 and Abil Quat 3474.

Further examples of said at least one aminosilicone include:

d) quaternary ammonium and polyalkylene oxide silicones wherein the quaternary nitrogen groups are located in the polysiloxane backbone, at the termini, or both.

Such silicones are described in PCT Publication No. WO 2002/010257, the disclosure of which is incorporated by reference herein.

Siliciones falling within this class are the silicones sold by the company Momentive under the names Silsoft Q . . . .

(e) Aminofunctional silicones having morpholino groups of formula (V):

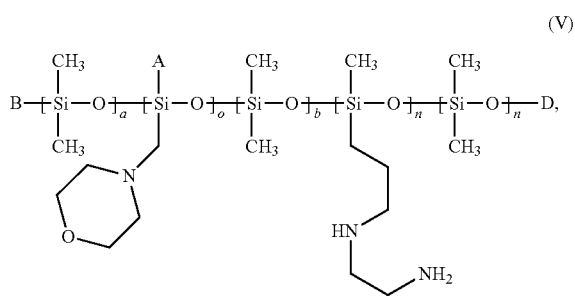

in which
A denotes a structural unit (I), (II), or (III) bound via —O—

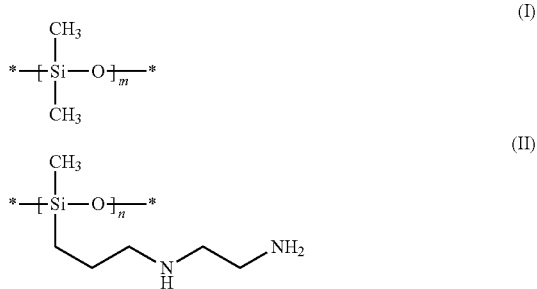

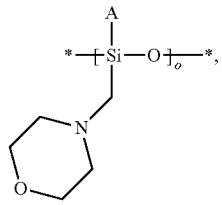

or an oligomeric or polymeric residue, bound via —O—, containing structural units of formulas (I), (II), or (III), or half of a connecting oxygen atom to a structural unit (III), or denotes —OH,

* denotes a bond to one of the structural units (I), (II), or (III), or denotes a terminal group B (Si-bound) or D (O-bound), B denotes an —OH, —O—Si(CH$_3$)$_3$, —O—Si(CH$_3$)$_2$OH, —O—Si(CH$_3$)$_2$OCH$_3$ group, D denotes an —H, —Si(CH$_3$)$_3$, —Si(CH$_3$)$_2$OH, —Si(CH$_3$)$_2$OCH$_3$ group, a, b, and c denote integers between 0 and 1000, with the provision that a+b+c>0, m, n, and o denote integers between 1 and 1000.

Aminofunctional silicones of this kind bear the INCI name: Amodimethicone/Morpholinomethyl Silsesquioxane Copolymer. A particularly suitable amodimethicone is the product having the commercial name Wacker Belsil® ADM 8301E.

Examples of such silicones are available from the following suppliers:

offered by the company Dow Corning:
  Fluids: 2-8566, AP 6087, AP 6088, DC 8040 Fluid, fluid 8822A DC, DC 8803 & 8813 polymer, 7-6030, AP-8104, AP 8201;
  Emulsions: CE-8170 AF Micro Emulsion, 2-8177, 2-8194 Microemulsion, 9224 Emulsion, 939, 949, 959, DC 5-7113 Quat Microemulsion, DC 5-7070 Emulsion, DC CE-8810, CE 8401 Emulsion, CE 1619, Dow Corning Toray SS-3551, Dow Corning Toray SS-3552;

offered by the company Wacker:
  Wacker Belsil ADM 652, ADM 656, 1100, 1600, 1650 (fluids) ADM 6060 (linear amodimethicone) emulsion; ADM 6057 E (branched amodimethicone) emulsion; ADM 8020 VP (micro emulsion); SLM 28040 (micro emulsion);

offered by the Company Momentive:
  Silsoft 331, SF1708, SME 253 & 254 (emulsion), SM2125 (emulsion), SM 2658 (emulsion), Silsoft Q (emulsion)

offered by the company Shin-Etsu:
  KF-889, KF-8675, KF-8004, X-52-2265 (emulsion);

offered by the Company Siltech Silicones:
  Siltech E-2145, E-Siltech 2145-35;

offered by the company Evonik Industries:
  Abil T Quat 60th

Some non-limiting examples of aminosilicones include the compounds having the following INCI names: Silicone Quaternium-1, Silicone Quaternium-2, Silicone Quaternium-3, Silicone Quaternium-4, Silicone Quaternium-5, Silicone Quaternium-6, Silicone Quaternium-7, Silicone Quaternium-8, Silicone Quaternium-9, Silicone Quaternium-10, Silicone Quaternium-11, Silicone Quaternium-12, Silicone Quaternium-15, Silicone Quaternium-16, Silicone Quaternium-17, Silicone Quaternium-18, Silicone Quaternium-20, Silicone Quaternium-21, Silicone Quaternium-22, Quaternium-80, as well as Silicone Quaternium-2 Panthenol Succinate and Silicone Quaternium-16/Glycidyl Dimethicone Crosspolymer.

In an embodiment, the aminosilicones can be supplied in the form of a nanoemulsion and include MEM 9049, MEM 8177, MEM 0959, MEM 8194, SME 253, and Silsoft Q.

In an embodiment, the one or more silicones may include dimethicones, and/or dimethiconols. The dimethiconols are hydroxyl terminated dimethylsilicones represented by the general chemical formulas

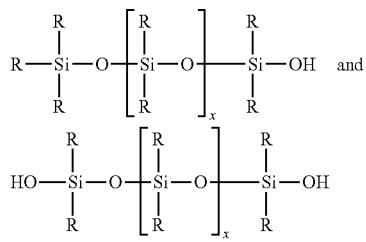

wherein R is an alkyl group (preferably R is methyl or ethyl, more preferably methyl) and x is an integer up to about 500, chosen to achieve the desired molecular weight. Commercial dimethiconols typically are sold as mixtures with dimethicone or cyclomethicone (e.g., Dow Coming® 1401, 1402, and 1403 fluids).

C. Emulsifiers

The concentrated hair care compositions described herein can comprise a combination of from about 1% to about 10%, alternatively from about 2% to about 9%, and alternatively from about 3% to about 8% of one or more Type I emulsifiers, by weight of the concentrated hair care composition; and from about 0.5% to about 5.0%, alternatively from about 0.6% to about 4.5%, and alternatively from about 0.8% to about 4.0% of one or more Type II emulsifiers, by weight of the concentrated hair care composition.

The Type I emulsifiers can be chosen from alcohol ethoxylates which are condensation products of aliphatic alcohols having from about 10 to about 15 carbon atoms, in either straight chain or branched chain configuration, with from about 5 to about 9 moles of ethylene oxide, e.g., a coconut alcohol ethylene oxide condensate having from about 5 to about 9 moles of ethylene oxide per mole of coconut alcohol, the coconut alcohol fraction having from about 10 to about 14 carbon atom. The aliphatic alcohol can be in the form of primary alcohol or secondary alcohol. The Type I emulsifiers have a HLB range from about 10.3 to about 13.5, alternatively from 10.3 to 13.5, alternatively from about 10.3 to about 13, alternatively from 10.3 to 13. The HLB (hydrophilic-lipophilic balance) of a surfactant is a measure of the degree to which it is hydrophilic or lipophilic.

The Type II emulsifiers can be chosen from alcohol ethoxylates which are condensation products of aliphatic alcohols having from about 10 to about 15 carbon atoms, in either straight chain or branched chain configuration, with from about 2 to about 4.9 moles of ethylene oxide, e.g., a coconut alcohol ethylene oxide condensate having from about 2 to about 4.9 moles of ethylene oxide per mole of coconut alcohol, the coconut alcohol fraction having from about 10 to about 14 carbon atom. The aliphatic alcohol could be in either form of primary alcohol or secondary alcohol. In an embodiment, the Type II emulsifiers could also have from about 2 to 4.9 moles of ethylene oxide, alternatively from 2 to 4.9 moles of ethylene oxide. The Type II emulsifiers have a HLB range from about 8 to about 10.3, alternatively from 8 to 10.3.

Optionally, the concentrated hair care compositions described herein can comprise one or more Type III emulsifiers which may be present at from about 0% to about 3%, alternatively from about 0.5% to about 2.5%, and alternatively from about 0.75% to about 1.5%, by weight of the concentrated hair care composition.

The Type III emulsifiers can be chosen from alcohol ethoxylates which are condensation products of aliphatic alcohols having from about 15 to about 20 carbon atoms, in either straight chain or branched chain configuration, with from about 20 to about 200 moles of ethylene oxide, e.g., cetearyl alcohol ethylene oxide condensate having from about 20 to about 200 moles of ethylene oxide per mole of cetearyl alcohol, the alcohol chain having predominantly C16 to C18 chain lengths. The Type III emulsifiers have an HLB range from about 16 to about 19.5, alternatively from 16 to 19.5, alternatively from about 16 to about 19. The addition of one or more Type III emulsifiers to the concentrated hair care compositions described herein can further enhance the stability of the concentrated hair care compositions described herein via steric interactions.

The LB value for an individual emulsifier can be calculated using the following example method:

A typical nonionic emulsifier (e.g. Laureth-4) comprises an ethylene oxide groups or polyhydric alcohol hydrophilic portions with a fatty alcohol hydrophobic portion. The HLB for a nonionic surfactant can be calculated as follows:

HLB = (Weight % of Hydrophile component) × 20

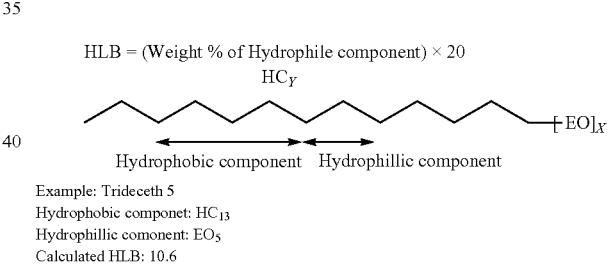

Example: Trideceth 5
Hydrophobic componet: $HC_{13}$
Hydrophillic comonent: $EO_5$
Calculated HLB: 10.6

Hydrophylic-Lipohylic Balance (HLB)

This value indicates the hydrophylic-lipophylic balance of a molecule and is calculated theoretically:

Ethoxylated fatty alcohols: $HLB =$ $$20 \times \left( \frac{\text{Moleculat weight of Hydrophilic part}}{\text{Molecular weight of molecule}} \right)$$

EXAMPLE 1

HLB Calculation For Laureth-4

Molecular weight of ethoxylate portion=176
Molecular weight of lauryl alcohol=186
Wt. % Hydrophile=(176/(176+186))×100=48.6%
HLB=20×48.6/100=9.7

EXAMPLE 2

Calculation of HLB For a Surfactant Mixture

The surfactant mixture is a 70/30 blend of Steareth-2 and Steareth-21.

Total HLB:

Steareth-2 contribution 0.7×4.9=3.43

Steareth-21 contribution 0.3×15.5=4.65

Total HLB=8.08

Some Exemplary Emulsifiers:

| C10 primary alcohol branched | | | |
|---|---|---|---|
| | HLB | HC chain length | Mw |
| Imbentin-E/100/030 (3 EO) | 8.5 | 10 | 290 |
| Imbentin-E/100/050 (5 EO) | 11.5 | 10 | 380 |
| Imbentin-E/100/060 (6 EO) | 12.5 | 10 | 420 |

| C13 primary alcohol branched | | | |
|---|---|---|---|
| | HLB | HC chain length | Mw |
| Imbentin-T/030 (3 EO) | 8.1 | 13 | 330 |
| Imbentin-T/040 (4 EO) | 9 | 13 | 380 |
| Imbentin-T/050 (5 EO) | 10.6 | 13 | 420 |
| Imbentin-T/060 (6 EO) | 11.5 | 13 | 460 |

| C11-15 Secondary alcohol | | | |
|---|---|---|---|
| | HLB | HC chain length | Mw |
| C11-15 Pareth-5 (5 EO) | 10.6 | 11-15 | 415 |
| C11-15 Pareth-7 (7 EO) | 12.1 | 11-15 | 515 |
| C11-15 Pareth-9 (9 EO) | 13.3 | 11-15 | 584 |
| C11-15 Pareth-12 (12 EO) | 14.5 | 11-15 | 738 |

The average HLB value for the combination of the one or more Type I emulsifiers and the one or more Type II emulsifiers in the emulsifier system is from about 9.25 to about 13.25, alternatively from 9.25 to 13.25 based on the mole average. The mole average HLB value for the emulsifier mixture ($HLB_{mix}$) is calculated via solving the two following equations, concurrently:

$$a: HLB_{mix} = \frac{w\,\%_{EmI}}{Mw_{EmI}} \times HLB_{EmI} + \frac{w\,\%_{EmII}}{Mw_{EmII}} \times HLB_{EmII}$$

$$b: \frac{w\,\%_{EmI}}{Mw_{EmI}} + \frac{w\,\%_{EmII}}{Mw_{EmII}} = 1$$

wherein $w\,\%_{EmI}$ is the weight percentage for emulsifier Type I, $Mw_{EmI}$ is the molecular weight for emulsifier Type I, $w\,\%_{EmII}$ is the weight percentage for emulsifier Type II, $Mw_{EmII}$ is the molecular weight for emulsifier Type II.

For a target $HLB_{mix}$, the required w % for each emulsifier type can be calculated, as described in the following table:

| Type | EO# | HLB | Mw | Target $HLB_{mix}$: 11 | Target $HLB_{mix}$: 12 |
|---|---|---|---|---|---|
| Trideceth 9[1] | EmI | 9 | 13.2 | 601 | 71% | 86% |
| Trideceth 3[2] | EmII | 3 | 8 | 333 | 29% | 14% |

[1]NOVEL TDA 9
[2]NOVEL TDA 3

D. Perfume

The concentrated hair care composition may comprise from about 1% to about 5%, alternatively from about 1.5% to about 4.5%, and alternatively from about 2% to about 4% perfume, by weight of the concentrated hair care composition.

In an embodiment, the concentrated hair care composition may have a silicone to perfume ratio of from about 95:5 to about 50:50, 90:10 to 60:40, 85:15 to 70:30.

Examples of suitable perfumes may be provided in the CTFA (Cosmetic, Toiletry and Fragrance Association) 1992 International Buyers Guide, published by CFTA Publications and OPD 1993 Chemicals Buyers Directory 80th Annual Edition, published by Schnell Publishing Co. A plurality of perfume components may be present in the concentrated hair care composition.

E. High Melting Point Fatty Compounds

The concentrated hair care composition may be substantially free of high melting point fatty compounds, alternatively less than about 1%, alternatively less than about 0.5%, alternatively less than about 0.25%, alternatively less than 0.1%, alternatively from about 0.01% to about 1%, alternatively 0% high melting point fatty compounds, by weight of the concentrated hair care composition. The concentrated hair care composition may have a oil to high melting point fatty compounds ratio of about 100:0 by weight of the oil and by weight of the high melting point fatty compounds.

The high melting point fatty compounds have a melting point of about 25° C. or higher, and are selected from the group consisting of fatty alcohols, fatty acids, fatty alcohol derivatives, fatty acid derivatives, and mixtures thereof. It is understood by the artisan that the compounds disclosed in this section of the specification can in some instances fall into more than one classification, e.g., some fatty alcohol derivatives can also be classified as fatty acid derivatives. However, a given classification is not intended to be a limitation on that particular compound, but is done so for convenience of classification and nomenclature. Further, it is understood by the artisan that, depending on the number and position of double bonds, and length and position of the branches, certain compounds having certain required carbon atoms may have a melting point of less than about 25° C. Such compounds of low melting point are not intended to be included in this section. Nonlimiting examples of the high melting point compounds are found in *International Cosmetic Ingredient Dictionary*, Fifth Edition, 1993, and *CTFA Cosmetic Ingredient Handbook*, Second Edition, 1992.

The fatty alcohols described herein are those having from about 14 to about 30 carbon atoms, preferably from about 16 to about 22 carbon atoms. These fatty alcohols are saturated and can be straight or branched chain alcohols. Nonlimiting examples of fatty alcohols include cetyl alcohol, stearyl alcohol, behenyl alcohol, and mixtures thereof.

The fatty acids useful herein are those having from about 10 to about 30 carbon atoms, preferably from about 12 to about 22 carbon atoms, and more preferably from about 16 to about 22 carbon atoms. These fatty acids are saturated and can be straight or branched chain acids. Also included are diacids, triacids, and other multiple acids which meet the requirements herein. Also included herein are salts of these fatty acids. Nonlimiting examples of fatty acids include lauric acid, palmitic acid, stearic acid, behenic acid, sebacic acid, and mixtures thereof.

The fatty alcohol derivatives and fatty acid derivatives useful herein include alkyl ethers of fatty alcohols, alkoxylated fatty alcohols, alkyl ethers of alkoxylated fatty alcohols, esters of fatty alcohols, fatty acid esters of compounds having esterifiable hydroxy groups, hydroxy-substituted fatty acids, and mixtures thereof. Nonlimiting examples of fatty alcohol derivatives and fatty acid derivatives include materials such as methyl stearyl ether; the ceteth series of compounds such as ceteth-1 through ceteth-45, which are ethylene glycol ethers of cetyl alcohol, wherein the numeric designation indicates the number of ethylene glycol moieties present; the steareth series of compounds such as steareth-1 through steareth-10, which are ethylene glycol ethers of steareth alcohol, wherein the numeric designation indicates the number of ethylene glycol moieties present; ceteareth 1 through ceteareth-10, which are the ethylene glycol ethers of ceteareth alcohol, i.e., a mixture of fatty alcohols containing predominantly cetyl and stearyl alcohol, wherein the numeric designation indicates the number of ethylene glycol moieties present; C16-C30 alkyl ethers of the ceteth, steareth, and ceteareth compounds just described; polyoxyethylene ethers of behenyl alcohol; ethyl stearate, cetyl stearate, cetyl palmitate, stearyl stearate, myristyl myristate, polyoxyethylene cetyl ether stearate, polyoxyethylene stearyl ether stearate, polyoxyethylene lauryl ether stearate, ethyleneglycol monostearate, polyoxyethylene monostearate, polyoxyethylene distearate, propyleneglycol monostearate, propyleneglycol distearate, trimethylolpropane distearate, sorbitan stearate, polyglyceryl stearate, glyceryl monostearate, glyceryl distearate, glyceryl tristearate, and mixtures thereof.

In an embodiment, the fatty compound may be a single high melting point compound of high purity. Single compounds of pure fatty alcohols selected may be selected from the group consisting of pure cetyl alcohol, stearyl alcohol, and behenyl alcohol. By "pure" herein, what is meant is that the compound has a purity of at least about 90%, alternatively at least about 95%.

Commercially available high melting point fatty compounds described herein include: cetyl alcohol, stearyl alcohol, and behenyl alcohol having tradenames KONOL series available from Shin Nihon Rika (Osaka, Japan), and NAA series available from NOF (Tokyo, Japan); pure behenyl alcohol having tradename 1-DOCOSANOL available from WAKO (Osaka, Japan), various fatty acids having tradenames NEO-FAT available from Akzo (Chicago, Ill. USA), HYSTRENE available from Witco Corp. (Dublin, Ohio USA), and DERMA available from Vevy (Genova, Italy).

F. Cationic Surfactants

In an embodiment, the concentrated hair care composition may comprise 0%, alternatively from about 0.25% to about 5%, alternatively from about 0.5% to about 4%, and alternatively from about 1% to about 3% cationic surfactants, by weight of the concentrated hair care composition.

The cationic surfactant may be a mono-long alkyl quaternized ammonium salt having the formula (XIII) [from WO2013148778]:

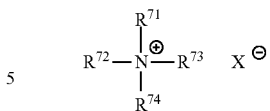

(XIII)

wherein one of $R^{71}$, $R^{72}$ $R^{73}$ and $R^{74}$ selected from an aliphatic group of from about 14 to about 30 carbon atoms or an aromatic, alkoxy, polyoxyalkylene, alkylamido, hydroxyalkyl, aryl or alkylaryl group having up to about 30 carbon atoms; the remainder of $R^{71}$, $R^{72}$ $R^{73}$ and $R^{74}$ are independently selected from an aliphatic group of from about 1 to about 8 carbon atoms or an aromatic, alkoxy, polyoxyalkylene, alkylamido, hydroxyalkyl, aryl or alkylaryl group having up to about 8 carbon atoms; and X is a salt-forming anion such as those selected from halogen, (e.g., chloride, bromide), acetate, citrate, lactate, glycolate, phosphate, nitrate, sulfonate, sulfate, alkylsulfate, glutamate, and alkyl sulfonate radicals. The aliphatic groups can contain, in addition to carbon and hydrogen atoms, ether linkages, and other groups such as amino groups. The longer chain aliphatic groups, e.g., those of about 16 carbons, or higher, can be saturated or unsaturated. Preferably, one of $R^{71}$, $R^{72}$ $R^{73}$ and $R^{74}$ is selected from an alkyl group of from about 14 to about 30 carbon atoms, more preferably from about 16 to about 22 carbon atoms, still more preferably from about 16 to about 18 carbon atoms; the remainder of $R^{71}$, $R^{72}$, $R^{73}$, and $R^{74}$ are independently selected from the group consisting of $CH_3$, $C_2H_5$, $C_2H_4OH$, $CH_2C_5H_5$, and mixtures thereof; and (X) is selected from the group consisting of Cl, Br, $CH_3OSO_3$, and mixtures thereof. It is believed that such mono-long alkyl quatemized ammonium salts can provide improved slippery and slick feel on wet hair.

Nonlimiting examples of such mono-long alkyl quatemized ammonium salt cationic surfactants include: behenyl trimethyl ammonium chloride available, for example, with tradename Genamine KDMP from Clariant, with tradename INCROQUAT TMC-80 from Croda and ECONOL TM22 from Sanyo Kasei; stearyl trimethyl ammonium chloride available, for example, with tradename CA-2450 from Nikko Chemicals; cetyl trimethyl ammonium chloride available, for example, with tradename CA-2350 from Nikko Chemicals; behenyltrimethylammonium methyl sulfate, available from FeiXiang; hydrogenated tallow alkyl trimethyl ammonium chloride; stearyl dimethyl benzyl ammonium chloride; and stearoyl amidopropyl dimethyl benzyl ammonium chloride.

Among them, more preferred cationic surfactants are those having a shorter alkyl group, i.e., $C_{16}$ alkyl group. Such cationic surfactant includes, for example, cetyl trimethyl ammonim chloride. It is believed that cationic surfactants having a shorter alkyl group are advantageous for concentrated hair care silicone nanoemulsion compositions of the present invention comprising a cationic surfactant and with improved shelf stability.

G. Water Miscible Solvents

The concentrated hair care compositions described herein may comprise from about 0.01% to about 25%, alternatively from about 0.01% to about 20%, and alternatively from about 0.01% to about 15% of a water miscible solvent, by weight of the concentrated hair care composition. In an embodiment, the concentrated hair care compositions described herein may comprise 0% of a water miscible solvent, by weight of the concentrated hair care composition. Non-limiting examples of suitable water miscible solvents include polyols, copolyols, polycarboxylic acids, polyesters and alcohols.

Examples of useful polyols include, but are not limited to, glycerin, diglycerin, propylene glycol, ethylene glycol, butylene glycol, pentylene glycol, 1,3-butylene glycol, cyclohexane dimethanol, hexane diol, polyethylene glycol (200-600), sugar alcohols such as sorbitol, manitol, lactitol and other mono- and polyhydric low molecular weight alcohols (e.g., $C_2$-$C_8$ alcohols); mono di- and oligo-saccharides such as fructose, glucose, sucrose, maltose, lactose, and high fructose corn syrup solids and ascorbic acid.

Examples of polycarboxylic acids include, but are not limited to citric acid, maleic acid, succinic acid, polyacrylic acid, and polymaleic acid.

Examples of suitable polyesters include, but are not limited to, glycerol triacetate, acetylated-monoglyceride, diethyl phthalate, triethyl citrate, tributyl citrate, acetyl triethyl citrate, acetyl tributyl citrate.

Examples of suitable dimethicone copolyols include, but are not limited to, PEG-12 dimethicone, PEG/PPG-18/18 dimethicone, and PPG-12 dimethicone.

Examples of suitable alcohols include, but are not limited to ethanol, n-propanol, isopropanol, n-butanol, sec-butanol, tert-butanol, n-hexanol and cyclohexanol.

Other suitable water miscible solvents include, but are not limited to, alkyl and allyl phthalates; napthalates; lactates (e.g., sodium, ammonium and potassium salts); sorbeth-30; urea; lactic acid; sodium pyrrolidone carboxylic acid (PCA); sodium hyraluronate or hyaluronic acid; soluble collagen; modified protein; monosodium L-glutamate; alpha & beta hydroxyl acids such as glycolic acid, lactic acid, citric acid, maleic acid and salicylic acid; glyceryl polymethacrylate; polymeric plasticizers such as polyquaterniums; proteins and amino acids such as glutamic acid, aspartic acid, and lysine; hydrogen starch hydrolysates; other low molecular weight esters (e.g., esters of $C_2$-$C_{10}$ alcohols and acids); and any other water soluble plasticizer known to one skilled in the art of the foods and plastics industries; and mixtures thereof.

In an embodiment, the water miscible solvents may be selected from the group consisting of glycerin, propylene glycol, dipropylene glycol, and mixtures thereof. EP 0283165 B1 discloses other suitable water miscible solvents, including glycerol derivatives such as propoxylated glycerol.

H. Viscosity Modifiers

The concentrated hair care composition described herein may comprise from about 0.001% to about 2%, alternatively from about 0.001% to about 1%, and alternatively from about 0.001% to about 0.5% of a viscosity modifier, by weight of the concentrated hair care composition. In an embodiment, the concentrated hair care composition described herein may comprise 0% of a viscosity modifier, by weight of the concentrated hair care composition. Non-limiting examples of suitable viscosity modifiers include water soluble polymers, cationic water soluble polymers, Examples of water soluble polymers include, but are not limited to (1) vegetable based polymers such as gum Arabic, tragacanth gum, galactan, guar gum, carob gum, karaya gum, carrageenan, pectin, agar, quince seed, algal colloid, starch (rice, corn, potato, or wheat), and glycyrrhizinic acid; (2) microorganism-based polymers such as xanthan gum, dextran, succinoglucan, and pullulan; and (3) animal-based polymers such as collagen, casein, albumin, and gelatin. Examples of semi-synthetic water-soluble polymers include (1) starch-based polymers such as carboxymethyl starch and methylhydroxypropyl starch; (2) cellulose-based polymers such as methylcellulose, nitrocellulose, ethylcellulose, methylhydroxypropylcellulose, hydroxyethylcellulose, sodium cellulose sulfate, hydroxypropylcellulose, sodium carboxymethylcellulose (CMC), crystalline cellulose, and cellulose powder; and (3) alginate-based polymers such as sodium alginate and propylene glycol alginate. Examples of synthetic water-soluble polymers include (1) vinyl-based polymers such as polyvinyl alcohol, polyvinyl methyl ether-based polymer, polyvinylpyrrolidone, and carboxyvinyl polymer (CARBOPOL 940, CARBOPOL 941; (2) polyoxyethylene-based polymers such as polyethylene glycol 20,000, polyethylene glycol 6,000, and polyethylene glycol 4,000; (3) copolymer-based polymers such as a copolymer of polyoxyethylene and polyoxypropylene, and PEG/PPG methyl ether; (4) acryl- based polymers such as poly(sodium acrylate), poly(ethyl acrylate), polyacrylamide, polyethylene imines, and cationic polymers. The water-swellable clay minerals are nonionic water-soluble polymers and correspond to one type of colloid-containing aluminum silicate having a triple layer structure. More particular, as examples thereof, mention may be made of bentonite, montmorillonite, beidellite, nontronite, saponite, hectorite, aluminum magnesium silicate, and silicic anhydride.

Examples of cationic water soluble polymers include, but are not limited to (1) quaternary nitrogen-modified polysaccharides such as cation-modified cellulose, cation-modified hydroxyethylcellulose, cation-modified guar gum, cation-modified locust bean gum, and cation-modified starch; (2) dimethyldiallylammonium chloride derivatives such as a copolymer of dimethyldiallylammonium chloride and acrylamide, and poly(dimethylmethylene piperidinium chloride); (3) vinylpyrrolidone derivatives such as a salt of a copolymer of vinylpyrrolidone and dimethylaminoethyl methacrylic acid, a copolymer of vinylpyrrolidone and methacrylamide propyltrimethylammonium chloride, and a copolymer of vinylpyrrolidone and methylvinylimidazolium chloride; and (4) methacrylic acid derivatives such as a copolymer of methacryloylethyldimethylbetaine, methacryloylethyl trimethylammonium chloride and 2-hydroxyethyl methacrylate, a copolymer of methacryloylethyldimethylbetaine, and methacryloylethyl trimethylammonium chloride and methoxy polyethylene glycol methacrylate.

I. Viscosity

The concentrated hair care composition described herein may have a liquid phase viscosity of from about 1 centipoise to about 80 centipoise, alternatively from about 3 to about 60 centipoise, alternatively from about 5 to about 45 centipoise, and alternatively from about 10 to about 40 centipoise. In one embodiment, the concentrated hair care composition described herein may have a liquid phase viscosity of from about 1 centipoise to about 150 centipoise, alternatively from about 2 centipoise to about 100 centipoise, alternatively from about 3 centipoise to about 60 centipoise, alternatively from about 5 centipoise to about 45 centipoise, and alternatively from about 10 centipoise to about 40 centipoise.

The viscosity values may be measured employing any suitable rheometer or viscometer at 25.0° C. and at a shear rate of about 2 reciprocal seconds. The viscosity values reported herein were measured using a TA Instruments AR-G2 Rheometer with a concentric cylinder attachment (cup with a diameter of 30.41 mm; a bob with a diameter of 27.98 mm and a length of 42.02 mm; and a concentric cylinder jacket assembly) at a shear rate of 2 reciprocal seconds at 25° C.

J. Optional Ingredients

The concentrated hair care composition described herein may optionally comprise one or more additional components known for use in hair care or personal care products, provided that the additional components are physically and chemically compatible with the essential components described herein, or do not otherwise unduly impair product stability, aesthetics or performance Such optional ingredients are most typically those materials approved for use in cosmetics and that are described in reference books such as the CTFA Cosmetic Ingredient Handbook, Second Edition, The Cosmetic, Toiletries, and Fragrance Association, Inc. 1988, 1992. Individual concentrations of such additional components may range from about 0.001 wt % to about 10 wt % by weight of the conditioning composition.

Emulsifiers suitable as an optional ingredient herein include mono- and di-glycerides, fatty alcohols, polyglycerol esters, propylene glycol esters, sorbitan esters and other emulsifiers known or otherwise commonly used to stabilized air interfaces, as for example those used during preparation of aerated foodstuffs such as cakes and other baked goods and confectionary products, or the stabilization of cosmetics such as hair mousses.

Further non-limiting examples of such optional ingredients include preservatives, perfumes or fragrances, cationic polymers, viscosity modifiers, coloring agents or dyes, conditioning agents, hair bleaching agents, thickeners, moisturizers, foam boosters, additional surfactants or nonionic cosurfactants, emollients, pharmaceutical actives, vitamins or nutrients, sunscreens, deodorants, sensates, plant extracts, nutrients, astringents, cosmetic particles, absorbent particles, adhesive particles, hair fixatives, fibers, reactive agents, skin lightening agents, skin tanning agents, anti-dandruff agents, perfumes, exfoliating agents, acids, bases, humectants, enzymes, suspending agents, pH modifiers, hair colorants, hair perming agents, pigment particles, anti-acne agents, anti-microbial agents, sunscreens, tanning agents, exfoliation particles, hair growth or restorer agents, insect repellents, shaving lotion agents, non-volatile solvents or diluents (water-soluble and water-insoluble), co-solvents or other additional solvents, and similar other materials.

K. Mechanical Foam Dispenser

The mechanical foam dispenser described herein may be selected from the group consisting of squeeze foam dispensers, pump foam dispensers, other mechanical foam dispensers, and combinations thereof. In an embodiment, the mechanical foam dispenser is a squeeze foam dispenser. Non-limiting examples of suitable pump dispensers include those described in WO 2004/078903, WO 2004/078901, and WO 2005/078063 and may be supplied by Albea (60 Electric Ave., Thomaston, Conn. 06787 USA) or Rieke Packaging Systems (500 West Seventh St., Auburn, Ind. 46706).

The mechanical foam dispenser may comprise a reservoir for holding the concentrated hair treatment composition. The reservoir may be made out of any suitable material selected from the group consisting of plastic, metal, alloy, laminate, and combinations thereof. The reservoir may be a refillable reservoir such as a pour-in or screw-on reservoir, or the reservoir may be for one-time use. The reservoir may also be removable from the mechanical foam dispenser. Alternatively, the reservoir may be integrated with the mechanical foam dispenser. In an embodiment, there may be two or more reservoirs.

In an embodiment, the reservoir may be comprised of a material selected from the group consisting of rigid materials, flexible materials, and combinations thereof. The reservoir may be comprised of a rigid material if it does not collapse under external atmospheric pressure when it is subject to an interior partial vacuum.

The concentrated hair care composition may be dispensed as a foam wherein the foam as a density of from about 0.025 g/cm$^3$ to about 0.30 g/cm$^3$, alternatively from about 0.035 g/cm$^3$ to about 0.25 g/cm$^3$, alternatively from about 0.045 g/cm$^3$ to about 0.20 g/cm$^3$, and alternatively from about 0.055 g/cm$^3$ to about 0.15 g/cm$^3$.

The concentrated hair care composition is dispensed at a dosage weight of from about 1 g to about 8 g, alternatively from about 1 g to about 7 g, alternatively from about 1 g to about 6 g, and alternatively from about 1 g to about 5 g. The dosage may be achieved by any manner of mechanical foaming as described above in either discrete or continuous foaming incidents. In the case of pump or squeeze foamers, the dosage may be achieved at from about 1 to about 10 pumps or squeezes, alternatively at from about 1 to about 7 pumps or squeezes, alternatively at from about 1 to about 5 pumps or squeezes, and alternatively at about 1 to about 3 pumps or squeezes. A continuous mechanical foamer may also include connection to a separate power source such as a battery or electrical outlet.

L. Water

The concentrated hair care composition described herein may comprise from about from about 60% to about 90% water, alternatively from about 65% to about 87.5%, alternatively from about 67.5% to about 85%, alternatively from about 70% to about 82.5%, and alternatively from about 72.5% to about 80% water.

Method of Treating Hair

The method of treating the hair described herein comprises (1) providing a concentrated hair care composition, as described herein, in a mechanical foam dispenser, (2) dispensing the concentrated hair care composition from the mechanical foam dispenser as a dosage of foam; (3) applying the foam to the hair; and (4) rinsing the foam from the hair.

EXAMPLES & DATA

The following examples and comparative examples are provided to help illustrate the concentrated hair care composition described herein. The exemplified compositions can be prepared by conventional formulation and mixing techniques. It will be appreciated that other modifications of the concentrated hair care compositions described herein within the skill of those in the emulsion formulation art can be undertaken without departing from the spirit and scope of this invention. All parts, percentages, and ratios herein are by weight unless otherwise specified. Some components may come from suppliers as dilute solutions. The amount stated reflects the weight percent of the active material, unless otherwise specified.

The emulsification route described herein is "Low-Energy Route" in which the aqueous emulsion in formed by phase inversion by composition (PIC)[1,2]. In this route water or acidified water is added to the mixture of silicone and emulsifiers.

[1]Salager et al.,J Disp. Sci & Tech. 4,313,83 [2]Sajjadi, Langmuir, 22,5597,2006

The concentrated hair care compositions described herein are of two types; one without gel network and the other with gel network.

The following tables describe comparative examples for the silicone emulsions prepared under the following conditions:

a. The emulsions containing only Type I emulsifier
b. The emulsions containing only Type II emulsifier
c. The emulsions containing Type I and Type I emulsifiers
d. The emulsions containing Type II and Type II emulsifiers Examples of Type I and Type II emulsifiers are provided below.

a. The emulsions containing only one Type I emulsifier

TABLE 1

| comparative example 1a | |
|---|---|
| Amodimethicone [1] | 20.00 |
| Trideceth 5 [2] | 10.00 |
| Glycerin | 0.00 |
| Water | Q.S. |
| pH | 9.8 |
| Particle Size (PS): 326 nm | |

[1] Y17045-Momentive
[2] Synpronic 13/5-LQ-(HLB: 11, EO: 5)

TABLE 2

| Comparative example 1b | |
|---|---|
| Amodimethicone [1] | 20.00 |
| Trideceth 5 [2] | 10.00 |
| Glycerin | 0.00 |
| Glacial acetic acid | 1.00 |
| Water | Q.S. |
| pH | 8.0 |
| Observation: Very high viscosity (Gelled) | |

[1] Y17045-Momentive
[2] Synpronic 13/5-LQ-(HLB: 11, EO: 5)

TABLE 3

| Comparative example 2a | |
|---|---|
| Amodimethicone [1] | 20.00 |
| C11-15 pareth 9 [2] | 10.00 |
| Glycerin | 0.00 |
| Glacial acetic acid | 1.00 |
| Water | Q.S. |
| PS: 249 nm | |

[1] Y17045-Momentive
[2] Tergitol 15-s-9 (HLB: 13.3, EO: 9)

TABLE 4

| Comparative example 2b | |
|---|---|
| Amodimethicone [1] | 20.00 |
| C11-15 pareth 9 [2] | 10.00 |
| Glycerin | 1.50 |
| Glacial acetic acid | 1.00 |
| Water | Q.S. |
| PS: 228 nm | |

[1] Y17045-Momentive
[2] Tergitol 15-s-9 (HLB: 13.3, EO: 9)

b. The emulsions containing only one Type II emulsifier

TABLE 5

| Comparative example 3 | |
|---|---|
| Amodimethicone [1] | 20.00 |
| Trideceth 3 [2] | 10.00 |
| Glycerin | 0.00 |
| Glacial acetic acid | 1.00 |
| Water | Q.S. |
| PS: 256 nm | |

[1] Y17045-Momentive
[2] Iconol TDA 3 (HLB: 8, EO: 3)

TABLE 6

| Comparative example 4 and 5 | | |
|---|---|---|
| Comparative Example | 4 | 5 |
| Amodimethicone [1] | 20.00 | 20.00 |
| Deceth 4 | 10.00 | 8.00 |
| Glycerin | 1.50 | 1.50 |
| Glacial acetic acid | 1.00 | 1.00 |
| Water | Q.S. | Q.S. |
| | PS: 287 nm | PS: 326 nm |

[1] Y17045-Momentive
2 Imbentin-E/100/040 (HLB: 10, EO: 4)

TABLE 7

| Comparative Example 6 | |
|---|---|
| Amodimethicone [1] | 20.00 |
| Laureth 4 [2] | 10.00 |
| Glycerin | 0.00 |
| Glacial acetic acid | 1.00 |
| Water | Q.S. |
| PS: 246 nm | |

[1] Y17045-Momentive
[2] Dehydol LS 4 DEO-N (HLB: 9, EO: 4)

c. The emulsions containing a combination of Type I emulsifiers

TABLE 8

| Comparative example 7 | |
|---|---|
| Amodimethicone [1] | 20.00 |
| C11-15 Pareth 7 [2] | 7.73 |
| C11-15 Pareth 9 [3] | 2.27 |
| Glycerin | 1.50 |
| Glacial acetic acid | 1.00 |
| Water | Q.S. |
| PS: 59 nm | |

[1] Y17045-Momentive
[2] Tergitol 15-s-9 (HLB: 13.3, Mw: 584 g/mol)
[3] Tergitol 15-s-7 (HLB: 12.1, Mw: 515 g/mol)

The emulsion given in comparative example 7 (Table 8), gives a particle size below 100 nm; however, once the emulsion is incorporated into the conditioner formulation given in the comparative example 8, the formulation becomes unstable as evidenced by the increase in the particle size.

TABLE 9

| Comparative Example 8 Conditioner without gel network | |
|---|---|
| Ingredient | % w |
| water | Q.S. |
| Cetrimonium Chloride [1] | 3.48 |
| Behentrimonium Chloride [2] | 1.85 |

TABLE 9-continued

Comparative Example 8
Conditioner without gel network

| Ingredient | % w |
|---|---|
| Distearyldimonium Chloride [3] | 1.07 |
| Aminosilicone emulsion - Comparative Example 7 | 60 |
| Glycerin | 10 |
| Kathon | 0.033 |
| Perfume | 3 |
| PS: 128 nm | |

[1] CTAC Varisoft 300
[2] Genamin KDMP (BTMAC)
[3] Varisoft TA100 d. The emulsions containing a combination of Type II emulsifiers

TABLE 10

Comparative examples 9-11

| Comparative Example | 9 | 10 | 11 |
|---|---|---|---|
| Amodimethicone [1] | 20.00 | 20.00 | 20.00 |
| Deceth 2 [2] | 0 | 0.44 | 0 |
| Deceth 2.5 [3] | 0.71 | 0.00 | 0.00 |
| Deceth 3 [4] | 0 | 0 | 0.88 |
| Deceth 4 [5] | 9.29 | 9.56 | 9.12 |
| Glycerin | 1.50 | 1.50 | 1.50 |
| Glacial acetic acid | 1.00 | 1.00 | 1.00 |
| Water | Q.S. | Q.S. | Q.S. |
| | PS: 239 nm | PS: 356 nm | PS: 294 nm |

[1] Y17045-Momentive
[2] Imbentin-AG/100/020 (HLB: 7.2, Mw: 240 g/mol)
[3] Greenbentin DE/025 (HLB: 8.2, Mw: 268 g/mol)
[4] Imbentin-E/100/030 (HLB: 8.5, Mw: 290 g/mol)
[5] Imbentin-E/100/040 (HLB: 10.0, Mw: 330 g/mol)

The following comparative examples describe the conditioner formulations without gel network.

TABLE 11

Comparative example 12 comprising a commercial emulsion using a combination of only Type I emulsifiers.

| Ingredient | % w |
|---|---|
| water | Q.S. |
| Cetrimonium Chloride [1] | 3.48 |
| Behentrimonium Chloride [2] | 1.85 |
| Distearyldimonium Chloride [3] | 1.07 |
| Aminosilicone emulsion (20% active) [4] | 60 |
| Glycerin | 10 |
| Kathon | 0.033 |
| Perfume | 3 |
| PS: 172 nm (after 2 weeks aging at 40° C.) | |

[1] CTAC Varisoft 300
[2] Genamin KDMP (BTMAC)
[3] Varisoft TA100 Silsoft 253 (INCI: Amodimethicone (and) C11-15 Pareth-7 (and)
[4] Laureth-9 (and) Glycerin (and) Trideceth-12)

TABLE 12

Comparative example 13 comprising a commercial emulsion using only a Type I emulsifier.

| Ingredient | % w |
|---|---|
| water | Q.S. |
| Cetrimonium Chloride [1] | 3.48 |
| Behentrimonium Chloride [2] | 1.85 |
| Distearyldimonium Chloride [3] | 1.07 |
| Amodimethicone/Morpholinomethyl Silsesquioxane Copolymer, Trideceth-5, Glycerin [4] | 60 |
| Glycerin | 10 |
| Kathon | 0.033 |
| Perfume | 3 |
| PS: 186 nm (after 2 weeks aging at 40° C.) | |

[1] CTAC Varisoft 300
[2] Genamin KDMP (BTMAC)
[3] Varisoft TA100
[4] ADM 8301

1. Conditioner Formulations Without Gel Network

The following examples (Tables 13 and 14) describe the conditioner formulations without gel network. The formulations comprise of previously prepared silicon emulsions with a combination of Type I and Type II emulsifiers with the appropriate HLB values (added into the conditioner formulation).

An example of the inventive emulsion containing a combination of Type I and Type II emulsifiers is provided below

TABLE 13A

Example 14A

| Ingredient | Amount |
|---|---|
| Amodimethicone [1] | 20 |
| C11-C15 Pareth 7 [2] | 6.64 |
| Deceth 3 [3] | 3.36 |
| Glycerin | 3 |
| Glacial acetic acid | To adjust the pH |
| Water (pH: 4-5) | Q.S. |

[1] Y17045-Momentive
[2] Tergitol 15-s-7 (HLB: 12.1, Mw: 515 g/mol)
[3] Imbentin-E/100/030 (HLB: 8.5, Mw: 290 g/mol)

TABLE 13B

Example 14B (using emulsion from Ex. 14A)

| Ingredient | % w |
|---|---|
| Water | Q.S. |
| Cetrimonium Chloride | 3.48 |
| Behentrimonium Chloride | 1.85 |
| Distearyldimonium Chloride | 1.07 |
| Amodimethicone [1] | 12 |
| C11-15 Pareth 7 [2] | 3.84 |
| Deceth-3 [3] | 2.16 |
| Glycerin | 11.8 |
| Kathon | 0.033 |
| Perfume | 3 |
| PS: 13 nm (after 2 weeks aging at 40° C.) | |

[1] Y17045-Momentive
[2] Tergitol 15-s-7 (HLB: 12.1, Mw: 515 g/mol)
[3] Imbentin-E/100/030 (HLB: 8.5, Mw: 290 g/mol)

TABLE 14

Examples 15 to 20

| Ingredient | 15 % w | 16 % w | 17 % w | 18 % w | 19 % w | 20 % w |
|---|---|---|---|---|---|---|
| Cetrimonium Chloride | 3.48 | 3.48 | 3.48 | 3.48 | 3.48 | 3.48 |
| Behentrimonium Chloride | 1.85 | 1.85 | 1.85 | 1.85 | 1.85 | 1.85 |
| Distearyldimonium Chloride | 1.07 | 1.07 | 1.07 | 1.07 | 1.07 | 1.07 |
| Amodimethicone[1] | 12 | 12 | 12 | 12 | 12 | 12 |
| C11-15 Pareth 7[2] | 3.84 | 3.28 | 3.28 | 0 | 0 | 0 |
| Trideceth-3[3] | 2.16 | 1.82 | 0 | 0 | 0.72 | 0 |
| Trideceth 5[4] | 0 | 0 | 0 | 4.38 | 4.38 | 0 |
| C12-13 Pareth-3[5] | 0 | 0 | 1.82 | 0.72 | 0 | 0 |
| Ceteareth 25[6] | 0 | 0 | 0.9 | 0 | 0.72 | 0 |
| Steareth 100[7] | 0 | 0.9 | 0 | 0.9 | 0 | 0 |
| C11-15 Pareth 5[8] | 0 | 0 | 0 | 0 | 0 | 3.28 |
| Tridedceth 4[9] | 0 | 0 | 0 | 0 | 0 | 1.18 |
| Glycerin | 11.8 | 11.8 | 11.8 | 11.8 | 11.8 | 11.8 |
| Kathon | 0.033 | 0.033 | 0.033 | 0.033 | 0.033 | 0.033 |
| Perfume | 3 | 3 | 3 | 3 | 3 | 3 |
| water | Q.S. | Q.S. | Q.S. | Q.S. | Q.S. | Q.S. |
| PS (in nm Z average using DLS) | 16 | 23 | 22 | 19 | 26 | 22 |

[1]Y17045-Momentive
[2]Tergitol 15-s-7 (HLB: 12.1, Mw: 515 g/mol)
[3]Iconol TDA 3 (HLB: 8, Mw: 333 g/mol)
[4]Novel TDA-5 (HLB: 10.4, Mw: 421 g/mol)
[5]Brij LT-3 (HLB: 8, Mw: 333 g/mol)
[6]Cremophor A 25 (HLB: 16.2, Mw: 1360 g/mol)
[7]Brij S100 (HLB: 18.8, 4670 g/mol)
[8]Tergitol 15-s-5 (HLB: 10.6, Mw: 415 g/mol)
[9]Imbentin T-40 (HLB: 9, Mw: 380 g/mol)

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of treating the hair, the method comprising:
   a) providing a concentrated hair care composition in a mechanical foam dispenser, wherein the concentrated hair care composition comprises:
      i) from about 1% to about 5% perfume, by weight of the concentrated hair care composition;
      ii) an emulsion comprising:
         a. an amodimethicone comprising a particle size from about 1 nm to about 100 nm;
         b. from about 1% to about 10% of a first alcohol ethoxylate, by weight of the concentrated hair care composition, comprising from about 5 to about 9 moles of ethoxylate and an HLB value of from about 10.3 to about 13;
         c. from about 0.5% to about 5% of a second alcohol ethoxylate, by weight of the concentrated hair care composition, comprising from about 2 to about 4.9 moles of ethoxylate and an HLB value of from about 8 to about 10.3;
      wherein the concentrated hair care composition comprises from about 3% to about 25% of the amodimethicone, by weight of the concentrated hair care composition;
      from about 60% to about 90% water, by weight of the concentrated hair care composition;
      wherein the concentrated hair care composition is substantially free of fatty alcohol selected from the group consisting of cetyl alcohol, stearyl alcohol, behenyl alcohol, and mixtures thereof;
      wherein the concentrated hair care composition has a liquid phase viscosity of from about 1 centipoise to about 80 centipoise;
   b) dispensing the concentrated hair care composition from the mechanical foam dispenser as a dosage of foam;
   c) applying the foam to the hair; and
   d) rinsing the foam from the hair;
      wherein the foam has a density of from about 0.025 g/cm$^3$ to about 0.3 g/cm$^3$ when dispensed from the mechanical foam dispenser.

2. The method of claim 1, wherein the concentrated hair care composition comprises from about 65% to about 87.5% water, by weight of the concentrated hair care composition.

3. The method of claim 1, wherein the particle size of the amodimethicone is from about 5 nm to about 80 nm.

4. The method of claim 1, wherein the particle size of the amodimethicone is from about 10 nm to about 60 nm.

5. The method of claim 1, wherein the concentrated hair care composition comprises from about 4% to about 20% of the amodimethicone, by weight of the concentrated hair care composition.

6. The method of claim 1, wherein the concentrated hair care composition comprises from about 5% to about 15% of the amodimethicone, by weight of the concentrated hair care composition.

7. The method of claim 1, wherein the concentrated hair care composition comprises from about 8% to about 15% of the amodimethicone, by weight of the concentrated hair care composition.

8. The method of claim 1, wherein the concentrated hair care composition comprises from about 8% to about 18% of the amodimethicone, by weight of the concentrated hair care composition.

9. The method of claim 1, wherein the concentrated hair care composition comprises 0% fatty alcohol, by weight of the concentrated hair care composition.

10. The method of claim 1, wherein the concentrated hair care composition comprises from about 1.5% to about 4.5% perfume, by weight of the concentrated hair care composition.

11. The method of claim 1, wherein the foam has a dosage weight of from about 1 g to about 5 g when dispensed from the mechanical foam dispenser.

12. The method of claim 1, wherein the density of the foam is from about 0.075 g/cm$^3$ to about 0.175 g/cm$^3$.

13. The method of claim 1, wherein the viscosity is from about 5 centipoise to about 45 centipoise.

14. The method of claim 1, wherein the viscosity is from about 10 centipoise to about 40 centipoise.

15. The method of claim 1 wherein the emulsion is formed by phase inversion by composition.

* * * * *